(12) United States Patent
Yan et al.

(10) Patent No.: US 11,990,241 B2
(45) Date of Patent: May 21, 2024

(54) APPARATUS FOR COLLAGEN EVALUATION AND PROGNOSTIC PREDICTION OF COLORECTAL CANCER AND STORAGE MEDIUM

(71) Applicant: SHENZHEN PEOPLE'S HOSPITAL, Shenzhen (CN)

(72) Inventors: Jun Yan, Shenzhen (CN); Shumin Dong, Shenzhen (CN); Botao Yan, Shenzhen (CN); Weisheng Chen, Shenzhen (CN); Xiaoyu Dong, Shenzhen (CN); Xiumin Liu, Shenzhen (CN); Shuhan Zhao, Shenzhen (CN); Jiaxin Cheng, Shenzhen (CN); Yanfeng Dong, Shenzhen (CN); Wei Jiang, Shenzhen (CN); Dexin Chen, Shenzhen (CN); Guoxin Li, Shenzhen (CN)

(73) Assignee: SHENZHEN PEOPLE'S HOSPITAL, Shenzhen (CN)

( * ) Notice: Subject to any disclaimer, the term of this patent is extended or adjusted under 35 U.S.C. 154(b) by 0 days.

(21) Appl. No.: 18/286,475

(22) PCT Filed: Nov. 15, 2022

(86) PCT No.: PCT/CN2022/131939
§ 371 (c)(1),
(2) Date: Oct. 11, 2023

(87) PCT Pub. No.: WO2023/168981
PCT Pub. Date: Sep. 14, 2023

(65) Prior Publication Data
US 2024/0096491 A1    Mar. 21, 2024

(30) Foreign Application Priority Data
Mar. 8, 2022 (CN) .......................... 202210218325.1

(51) Int. Cl.
*G06T 7/00* (2017.01)
*G06V 10/25* (2022.01)
(Continued)

(52) U.S. Cl.
CPC ........... *G16H 50/20* (2018.01); *G06T 7/0012* (2013.01); *G06V 10/25* (2022.01); *G06V 10/44* (2022.01);
(Continued)

(58) Field of Classification Search
CPC . G06T 7/0012; G06T 7/11; G06T 7/12; G06T 7/187; G06T 2207/30028;
(Continued)

(56) References Cited

U.S. PATENT DOCUMENTS

| 10,229,488 B2 * | 3/2019 | Yu et al. ............... G06T 7/0012 |
| 2008/0015448 A1 * | 1/2008 | Keely et al. ......... A61B 5/0068 600/562 |

(Continued)

FOREIGN PATENT DOCUMENTS

| CN | 107941760 A | 4/2018 |
| CN | 110391015 A | 10/2019 |

(Continued)

OTHER PUBLICATIONS

PCT/CN2022/131939 International Search Report of the International Searching Authority, dated Feb. 9, 2023, 3 pages in English and 3 pages in Chinese.
(Continued)

Primary Examiner — Andrew W Johns
(74) Attorney, Agent, or Firm — Nolte Lackenbach Siegel

(57) ABSTRACT

A computer readable storage medium is provided. When contents of the computer readable storage medium are executed by a processor, multi-photon imaging may be performed on a histopathological section containing tumor
(Continued)

environment information, and pathological partitioning of a tumor microenvironment may be further performed through image processing. A value of each collagen feature parameters, such as a morphological feature parameter, an energy feature parameter and a texture feature parameter, may be extracted from a tumor tissue region, an invasive margin (IM) region and a normal tissue (N) region. An inter-region difference and a variation may be calculated according to feature parameters of regions. A collagen feature scoring model may be established. A collagen feature score may be calculated with the collagen feature parameters input to the model.

12 Claims, 3 Drawing Sheets

(51) Int. Cl.
*G06V 10/44* (2022.01)
*G16H 50/20* (2018.01)
(52) U.S. Cl.
CPC ............... *G06T 2207/30028* (2013.01); *G06T 2207/30096* (2013.01)

(58) Field of Classification Search
CPC .......... G06T 2207/30096; G06V 10/25; G06V 10/26; G06V 10/267; G06V 10/44; G06V 10/72; G16H 30/00; G16H 30/40; G16H 50/20
See application file for complete search history.

(56) References Cited

U.S. PATENT DOCUMENTS

2020/0234442 A1 7/2020 Barnes et al.
2021/0052212 A1* 2/2021 Yaroslavsky et al. ...................... A61B 5/0066

FOREIGN PATENT DOCUMENTS

| CN | 113234829 A | 8/2021 |
| CN | 114299069 A | 4/2022 |

OTHER PUBLICATIONS

Notification of Grant for Parent-Priority China No. 202210218325.1 Dated: Apr. 22, 2022; 2 pages in English and 3 pages in Chinese.

* cited by examiner

Acquire a multi-photon imaging image of a target imaging region in a histopathological section, and perform image processing on the multi-photon imaging image to partition the multi-photon imaging image into a CT region, an IM region and an N region — 110

Extract a value of each collagen feature parameter in each region, and calculate scoring parameters according to the value of each collagen feature parameter, where the scoring parameters include a mean of each collagen feature parameter in each region, an inter-region difference value and a variation value — 120

Select the scoring parameters corresponding to target collagen features for collagen feature score calculation, thereby obtaining a collagen feature score of the histopathological section — 130

FIG. 1

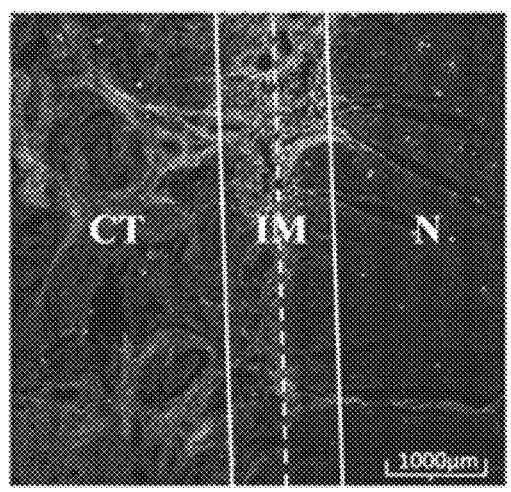

FIG. 2

APPARATUS FOR COLLAGEN EVALUATION AND PROGNOSTIC PREDICTION OF COLORECTAL CANCER AND STORAGE MEDIUM

CROSS REFERENCE TO RELATED APPLICATIONS

This application is a national stage of International Application No. PCT/CN2022/131939 filed on Nov. 15, 2022, which claims priority to Chinese Patent Application 202210218325.1 filed with the China National Intellectual Property Administration on Mar. 8, 2022, and entitled "APPARATUS FOR COLLAGEN EVALUATION AND PROGNOSTIC PREDICTION OF COLORECTAL CANCER AND STORAGE MEDIUM" Both of the aforementioned applications are hereby incorporated by reference in their entireties.

TECHNICAL FIELD

The present disclosure relates to the field of medical imaging technology, and in particular, to an apparatus for collagen evaluation and prognostic prediction of colorectal cancer and a storage medium.

BACKGROUND

Colorectal cancer is one of the most common malignant tumors worldwide, and in recent years, the incidence of the colorectal cancer has shown a significant upward trend. A tumor node metastasis (TNM) staging system in colorectal cancer prediction and determination is the most widely used clinical method for collagen evaluation and prognostic prediction at present, i.e., evaluating and staging a tumor by evaluating conditions of tumor, nodes and metastasis and then predicting prognosis.

However, the TNM staging system still has certain limitations. On the one hand, there is a difference in clinical outcomes of patients at a same stage after receiving similar therapeutic regimens, and in stage II colorectal cancer and stage III colorectal cancer, this difference is more prominent. On the other hand, a TNM staging apparatus focuses on the own features of a tumor, but lacks evaluation on a tumor microenvironment "soil". Therefore, it is necessary to further supplement a prognostic strategy based on the tumor microenvironment.

SUMMARY

An objective of embodiments of the present disclosure is to provide an apparatus for collagen evaluation and prognostic prediction of colorectal cancer and a storage medium so that the above-mentioned problems can be improved.

Embodiments of the present disclosure are achieved as follows.

In one aspect, the present disclosure provides a computer readable storage medium storing a computer program, where the computer program includes program instructions that, when executed by a processor, cause the processor to perform the following steps:

acquiring a multi-photon imaging image of a target imaging region in a histopathological section, and performing image processing on the multi-photon imaging image to partition the multi-photon imaging image into a center of tumor (CT) region, an invasive margin (IM) region and a normal tissue (N) region;

extracting a value of each collagen feature parameter in each region, and calculating scoring parameters according to the value of each collagen feature parameter, where the scoring parameters include a mean of each collagen feature parameter in each region, an inter-region difference value and a variation value, where the inter-region difference value is a difference between means of each collagen feature parameter of any two regions, and the variation value is a ratio of two inter-region difference values, and selecting the scoring parameters corresponding to target collagen features for collagen feature score calculation, thereby obtaining a collagen feature score of the histopathological section; and performing prognostic prediction in combination with TNM staging information of a patient and the collagen feature score.

It will be understood that the present disclosure provides a computer readable storage medium. When contents of the computer readable storage medium are executed by a processor, multi-photon imaging may be performed on a histopathological section containing tumor environment information, and pathological partitioning of a tumor microenvironment may be further performed through image processing. A value of each collagen feature parameter, such as a morphological feature parameter, an energy feature parameter and a texture feature parameter, may be extracted from a tumor tissue region, an invasive margin (IM) region and a normal tissue (N) region. An inter-region difference and a variation may be calculated according to the feature parameters of the regions. A collagen feature scoring model may be established, and a collagen feature score may be calculated with the collagen feature parameters input to the model. The collagen feature score may well make up for a lack of evaluation of a TNM staging system on the tumor microenvironment "soil" and provide a reference for prognostic prediction of colorectal cancer more effectively.

In an alternative embodiment of the present disclosure, the performing image processing on the multi-photon imaging image to partition the multi-photon imaging image into a CT region, an IM region and an N region may include:
  extracting a boundary line between a tumor and a normal tissue, and determining a region containing the tumor as an initial CT region and a region containing the normal tissue as an initial N region;
  translating the boundary line toward the initial CT region by a first distance to form a first boundary line, and translating the boundary line toward the initial N region by a second distance to form a second boundary line;
  determining a region between the first boundary line and the second boundary line as the IM region; and
  determining a region in the initial CT region other than the IM region as the CT region and a region in the initial N region other than the IM region as the N region.

In an alternative embodiment of the present disclosure, the extracting a value of each collagen feature parameter in each region, and calculating scoring parameters according to the value of each collagen feature parameter may include:
  randomly selecting three CT subregions ROI1, ROI2 and ROI3 in the CT region, and calculating an average value of values of each collagen feature parameter for the three CT subregions as a mean of the corresponding collagen feature parameter of the CT region;
  randomly selecting three IM subregions ROI4, ROI5 and ROI6 in the IM region, and calculating an average value of values of each collagen feature parameter for the three IM subregions as a mean of the corresponding collagen feature parameter of the IM region; and randomly selecting three N subregions ROI7, ROI8 and ROI9 in the N region, and calculating an average value of values of each collagen feature parameter for the three N subregions as a mean of the corresponding collagen feature parameter of the N region.

The extracting a value of each collagen feature parameter in each region, and calculating scoring parameters according to the value of each collagen feature parameter may further include:

calculating a difference between means of each collagen feature parameter for the CT region and the IM region as a first inter-region difference value;

calculating a difference between means of each collagen feature parameter for the IM region and the N region as a second inter-region difference value;

calculating a difference between means of each collagen feature parameter for the CT region and the N region as a third inter-region difference value; and deeming a ratio of the first inter-region difference value to the third inter-region difference value as an inter-region variation value.

It will be understood that the calculation of the inter-region difference value and the inter-region variation value is conducive to analyzing the collagen features of the tumor microenvironment multi-dimensionally. When the inter-region variation value is less than or equal to 1, it indicates that changing from the CT region to the IM region to the N region in the tumor microenvironment shows a same trend and the inter-region variation is low. When the inter-region variation value is greater than 1, it indicates that changing from the CT region to the IM region to the N region in the tumor microenvironment does not show a same trend and the inter-region variation is high.

In an alternative embodiment of the present disclosure, the selecting the scoring parameters corresponding to target collagen features for collagen feature score calculation may include:

establishing a collagen feature scoring model through a least absolute shrinkage and selection operator (LASSO) regression algorithm as follows:

$$Cf_{score} = \sum_{i=1}^{k} coef_i \cdot collagen\_feature_i;$$

where $Cf_{score}$ represents the collagen feature score; $collagen\_feature_i$, represents a scoring parameter corresponding to an ith target collagen feature; $coef_i$ represents a calculation coefficient corresponding to the parameter $collagen\_feature_i$; and k represents a number of the target collagen features.

In a second aspect, the present disclosure provides an apparatus for collagen evaluation and prognostic prediction of colorectal cancer, including a processor, an input device, an output device and a memory that are connected to one another, where the memory includes the computer readable storage medium as described in the first aspect of the present disclosure, and the processor is configured to call the program instructions.

Beneficial Effects are as Follows.

The present disclosure provides a computer readable storage medium. When contents of the computer readable storage medium are executed by a processor, multi-photon imaging may be performed on a histopathological section containing tumor environment information, and pathological partitioning of a tumor microenvironment may be further performed through image processing. A value of each collagen feature parameter, such as a morphological feature parameter, an energy feature parameter and a texture feature parameter, may be extracted from a tumor tissue region, an invasive margin (IM) region and a normal tissue (N) region. An inter-region difference and a variation may be calculated according to the features of the regions. A collagen feature scoring model may be established, and a collagen feature score may be calculated with the collagen feature parameters input to the model. The collagen feature score may well make up for a lack of evaluation of a TNM staging system on the tumor microenvironment "soil" and provide a reference for prognostic prediction of colorectal cancer more effectively.

The calculation of the inter-region difference value and the inter-region variation value is conducive to analyzing the collagen features of the tumor microenvironment multi-dimensionally. When the inter-region variation value is less than or equal to 1, it indicates that changing from the CT region to the IM region to the N region in the tumor microenvironment shows a same trend and the inter-region variation is low. When the inter-region variation value is greater than 1, it indicates that changing from the CT region to the IM region to the N region in the tumor microenvironment does not show a same trend and the inter-region variation is high.

In order to make the above objective, features, and advantages of the present disclosure clearer and more understandable, the present disclosure is described in detail below with optional embodiments and the accompanying drawings.

BRIEF DESCRIPTION OF THE DRAWINGS

To describe the technical solutions in the embodiments of the present disclosure more clearly, the accompanying drawings required in the embodiments will be briefly described below. It should be understood that, the following accompanying drawings show merely some of the embodiments of the present disclosure, and therefore should not be regarded as a limitation to the scope. A person of ordinary skill in the art may still derive other related drawings from these accompanying drawings without creative efforts.

FIG. 1 is a flowchart of program instructions stored on a computer readable storage medium provided in the present disclosure;

FIG. 2 is a schematic diagram of partitioning a multi-photon imaging image according to the present disclosure;

DETAILED DESCRIPTION OF THE EMBODIMENTS

Figure 3:
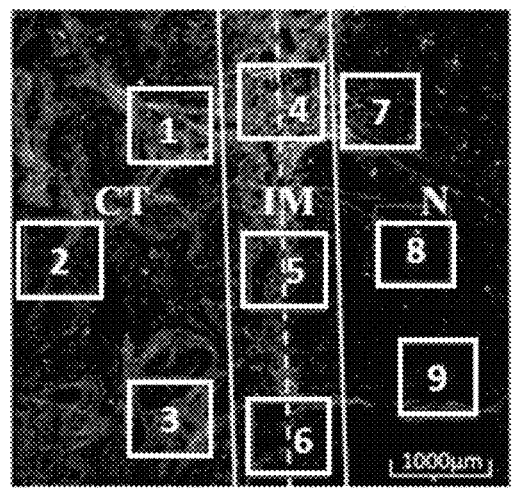
FIG. 3 is a schematic diagram illustrating a principle for calculating a mean of a collagen feature parameter according to the present disclosure.

The technical solutions in the embodiments of the present disclosure are clearly and completely described below with reference to the drawings in the embodiments of the present disclosure. Apparently, the described embodiments are merely some rather than all of the embodiments of the present disclosure. All other embodiments derived from the embodiments of the present disclosure by a person of ordinary skill in the art without creative efforts shall fall within the protection scope of the present disclosure.

A TNM staging system is a most universal international tumor staging system. The TNM staging system has become a standard means for clinicians and medical scientists to stage malignant tumors, i.e., evaluating and staging a tumor by evaluating conditions of primary tumor, involved lymph nodes and distant metastasis and then predicting prognosis.

However, the TNM staging system still has certain limitations. On the one hand, there is a difference in clinical outcomes of patients at a same stage after receiving similar therapeutic regimens, and in stage II colorectal cancer and stage III colorectal cancer, this difference is more prominent. On the other hand, a tumor is not merely a set of tumor cells and further includes various matrix cells, immune cells and a tumor microenvironment composed of an extracellular matrix and microvessels. Malignant tumor cells are equivalent to "seeds", and the tumor microenvironment is equivalent to "soil". The TNM staging system focuses on the own features of the tumor, but lacks evaluation on the tumor microenvironment "soil". Therefore, it is necessary to further supplement a prognostic strategy based on the tumor microenvironment.

In the first aspect, as shown in FIG. 1, the present disclosure provides a computer readable storage medium storing a computer program, where the computer program includes program instructions that, when executed by a processor, cause the processor to perform the following steps 110-130.

In step 110, a multi-photon imaging image for a target imaging region of a histopathological section is acquired, and image processing is performed on the multi-photon imaging image to partition the multi-photon imaging image into a CT region, an IM region and an N region.

To well make up for the lack of evaluation of the TNM staging system on the tumor microenvironment "soil", the target imaging region of the above-mentioned histopathological section is required to be a region at a tumor boundary. A method of acquiring the above-mentioned histopathological section includes: preparing a conventional pathological wax block from a surgical specimen of colorectal cancer, selecting a wax block at the tumor boundary, continuously slicing the wax block to obtain two sections each having a thickness of 4 μm, and subjecting a first section to hematoxylin-eosin staining (HE) dyeing and using a second section as the histopathological section for multi-photon imaging. A method of determining the above-mentioned target imaging region includes: scanning the first section at 20× using a digital section scanning system PRECICE 600, selecting a tumor boundary region having a great infiltration depth as the boundary region; and determining a region of the second section that corresponds to the boundary region as the target imaging region, where a size of the target imaging region is generally chosen to be 5 mm*5 mm.

The above-mentioned multi-photon imaging image may be acquired by scanning the target imaging region at 20× using Zeiss LSM 880 with Airyscan multi-photon confocal laser scanning system.

Multi-photon imaging is a multi-photon microscopic imaging technology based on nonlinear optics and femtosecond laser, which realizes imaging by utilizing own intrinsic autofluorescence of living tissue cells and second harmonics generated by the collagen and can directly obtain histological features of collagen in tissues and cells without dyeing. Matrix collagen is an important component of the microenvironment structure of a tumor, and is involved in a plurality of processes of tumor genesis and progression and affects prognosis, and a high collagen content in the tumor microenvironment is related to poor prognosis.

As shown in FIG. 2, ZEN software (Zen 2.3 lite, Carl Zeiss Microscopy GmbH, 2011) performs partitioning of the CT region, the N region and the IM region as described above.

In step 120, a value of each collagen feature parameter in each region is extracted, and each scoring parameter is calculated according to the value of the collagen feature parameter, where the scoring parameters include a mean of each collagen feature parameter in each region, an inter-region difference value and a variation value.

The inter-region difference value is a difference between means of each collagen feature parameter for any two regions, and the variation value is a ratio of two inter-region difference values.

Extraction of the value of each collagen feature parameter in each region may be completed by Matlab R2015b (MathWorks) software. Generally, 142 collagen feature parameters, including 8 morphological feature parameters, 6 intensity feature parameters and 128 texture feature parameters, may be extracted from the above-mentioned multi-photon imaging image.

The morphological feature parameters of the collagen include a fiber area, a fiber number, a fiber length, a fiber width, a fiber straightness, a fiber crosslink density, a fiber crosslink space and a fiber orientation.

The intensity feature parameters of the collagen are analyzed by a histogram and include: a histogram mean, a histogram variance, a histogram skewness, a histogram kurtosis, a histogram energy and a histogram entropy.

The structure feature parameters of the collagen include 80 gray-level co-occurrence matrix (GLCM)-based texture parameters and 48 Gabor wavelet transform parameters. The above-mentioned 80 GLCM-based texture parameters are calculated by calculating contrasts, correlations, energies and homogeneities of five pixels at displacements No. 1, No. 2, No. 3, No. 4 and No. 5 in four different angles of 0°, 45°, 900 and 135°. The 48 Gabor wavelet transform parameters are obtained from means and variances of four different dimensions and five different directions.

For the calculation of the mean of each collagen feature parameters in each region, as shown in FIG. 3, a region of interest (ROI) may be selected by ZEN software (Zen 2.3 lite, Carl Zeiss Microscopy GmbH, 2011). Three ROIs are randomly selected in each of the CT region, the IM region and the N region, and total 9 ROIs are obtained, each ROI having a size of 844 pixels×844 pixels (about 700 μm×700 μm). Subsequently, an average value of three values for each parameter of 142 collagen feature parameters extracted from the three ROIs in each of the CT region, the IM region and the N region is calculated as the mean of the corresponding collagen feature parameter of the region. An inter-region difference and a variation are calculated according to the features of the regions.

In step 130, a scoring parameter corresponding to a target collagen feature is selected for collagen feature score calculation, thereby obtaining a collagen feature score of the histopathological section.

Figure 5:
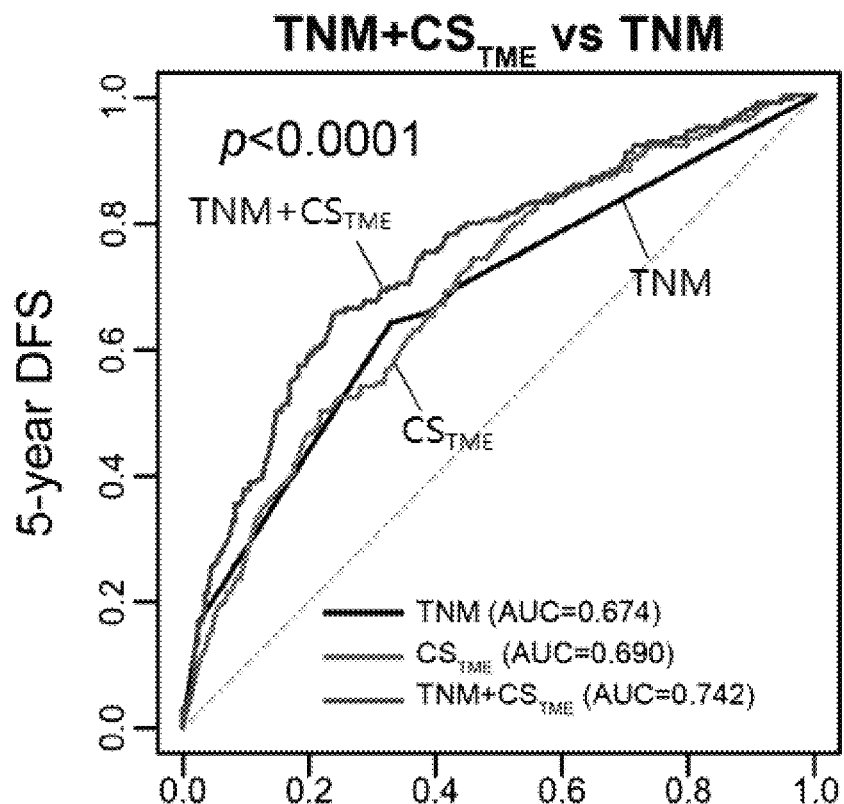
FIG. 5 is a schematic diagram of receiver operating characteristic (ROC) curves obtained by a method for collagen evaluation and prognostic prediction of colorectal cancer provided in the present disclosure and a method for collagen evaluation and prognostic prediction using a TNM staging system.

FIG. 5 is a schematic diagram illustrating receiver operating characteristic (ROC) curves obtained by the computer readable storage medium provided in the present disclosure and by the method for collagen evaluation and prognostic prediction using the TNM staging system. An ROC curve is also referred to as a sensitivity curve in that different points in the curve reflects the same sensitivity, which are responses to the same signal stimulus, but render results obtained under several different criteria. The ROC curves are a coordinate graph with false alarm probability as the horizontal axis and hit probability as the vertical axis and are curves drawn with different results obtained from a subject under a specific stimulus condition using different criteria. Area under curve (AUC) is defined as an area defined by the ROC curve and a coordinate axis, and it is apparent that the value of the area may not be greater than 1. Besides, since the ROC curve is usually above the straight line y=x, a value range of the AUC is between 0.5 and 1. The closer to 1.0 the AUC is, the higher the authenticity of the detection method is. When the AUC is equal to 0.5, the authenticity is the lowest without application value.

As can be seen from FIG. 5, the AUC of the 5-year disease free survival (DFS) of a patient obtained by the method for collagen evaluation and prognostic prediction using the TNM staging system is only 0.674 (as shown by the line TNM in FIG. 5); and the AUC of the 5-year DFS of the patient obtained by the computer readable storage medium provided in the present disclosure is significantly increased to 0.742 (as shown by the line TNM+$CS_{TME}$ in FIG. 5). Thus it can be seen that the computer readable storage medium provided in the present disclosure has higher prediction efficiency.

It will be understood that the present disclosure provides a computer readable storage medium. According to the method, multi-photon imaging is performed on a histopathological section containing environment information of a tumor, and pathological partitioning of a tumor microenvironment is further performed through image processing. A value of each collagen feature parameter, such as a morphological feature parameter, an energy feature parameter and a texture feature parameter, is extracted from a tumor tissue region, an IM region and an N region. An inter-region difference and a variation are calculated according to the features of the regions. A collagen feature scoring model is established, and a collagen feature score is calculated with the collagen feature parameters input to the model. The collagen feature score may well make up for a lack of evaluation of a TNM staging system on the tumor microenvironment "soil" and provide a reference for prognostic prediction of colorectal cancer more effectively.

In an alternative embodiment of the present disclosure, the step of performing image processing on the multi-photon imaging image to partition the multi-photon imaging image into a CT region, an IM region and an N region may be completed by the ZEN software (Zen 2.3 lite, Carl Zeiss Microscopy GmbH, 2011). The step specifically includes the following steps 111-114.

In step 111, a boundary line between a tumor and a normal tissue is extracted, and a region containing the tumor is determined as an initial CT region and a region containing the normal tissue as an initial N region.

The boundary line between the tumor and the normal tissue may be extracted by an image algorithm, as shown by the dotted line in FIG. 2, where the above-mentioned initial CT region is on the left side of the dotted line, and the above-mentioned initial N region is on the right side of the dotted line.

In step 112, the boundary line is translated toward the initial CT region by a first distance to form a first boundary line, and the boundary line is translated toward the initial N region by a second distance to form a second boundary line.

Generally, the boundary line may be translated toward the initial CT region by 500 µm to form the first boundary line L1 (as shown in FIG. 2), and the boundary line may be translated toward the initial N region by 500 µm to form the second boundary line L2 (as shown in FIG. 2).

In step 113, a region between the first boundary line and the second boundary line is determined as the IM region.

The region is as shown by the IM region in FIG. 2.

In step 114, a region in the initial CT region other than the IM region is determined as the CT region and a region in the initial N region other than the IM region is determined as the N region.

The regions are as shown by the CT region and the N region in FIG. 2.

In an alternative embodiment of the present disclosure, step 120 specifically includes the following steps 121-124.

In step 121, a difference between means of each collagen feature parameter for the CT region and IM region is calculated as a first inter-region difference value.

In step 122, a difference between means of each collagen feature parameter for the IM region and N region is calculated as a second inter-region difference value.

In step 123, a difference between means of each collagen feature parameter for the CT region and N region is calculated as a third inter-region difference value.

In step 124, a ratio of the first inter-region difference value to the third inter-region difference value is deemed as an inter-region variation value.

It will be understood that the calculation of the inter-region difference value and the inter-region variation value is conducive to analyzing the collagen features of the tumor microenvironment multi-dimensionally. When the inter-region variation value is less than or equal to 1, it indicates that changing from the CT region to the IM region to the N region in the tumor microenvironment shows a same trend and the inter-region variation is low. When the inter-region variation value is greater than 1, it indicates that changing from the CT region to the IM region to the N region in the tumor microenvironment does not show a same trend and the inter-region variation is high.

In an alternative embodiment of the present disclosure, step 130 specifically includes the following steps.

A collagen feature scoring model is established through a LASSO regression algorithm as follows:

$$Cf_{score} = \sum_{i=1}^{k} coef_i \cdot \text{collagen\_feature}_i;$$

where $Cf_{score}$ represents the collagen feature score; collagen_feature$_i$ represents the scoring parameter corresponding to the ith target collagen feature; $coef_i$ represents a calculation coefficient corresponding to the parameter collagen_feature$_i$; and k represents the number of the target collagen features.

In the above formula, k=16:
collagen_feature$_1$ represents a fiber area of the IM region, and $coef_1$ is 0.181.
collagen_feature$_2$ represents a fiber number of the IM region, and $coef_2$ is 0.081;
collagen_feature$_3$ represents a fiber length of the IM region, and $coef_3$ is 0.303;
collagen_feature$_4$ represents a fiber orientation of the N region, and $coef_4$ is −0.515;

collagen_feature$_5$ represents the first inter-region difference value of a fiber crosslink density, and co; is −0.126;

collagen_feature$_6$ represents a correlation for a pixel displacement of 3 and in an angle of 0° in a gray-level co-occurrence matrix of the CT region, and coef$_6$ is 0.018;

collagen_feature$_7$ represents a mean of image convolution of a coef$_6$ filter with a scale of 3 and an angle of 60° for the CT region, and coef$_7$ is 0.477;

collagen_feature$_8$ represents a mean of image convolution of a Gabor filter with a scale of 1 and an angle of 60° for the IM region, and Coef$_8$ is −0.119;

collagen_feature$_9$ represents a mean of image convolution of a Gabor filter with a scale of 3 and an angle of 600 for the IM region, and Coef$_9$ is 0.232;

collagen-feature$_{10}$ represents the third inter-region difference value of a variance of image convolution of a Gabor filter with a scale of 3 and an angle of 60°, and coef$_{10}$ is 0.016;

collagen_feature$_{11}$ represents the first inter-region difference value of a contrast for a pixel displacement of 3 and in an angle of 450 in a gray-level co-occurrence matrix, and coef$_{11}$ is 0.141;

collagen-feature$_{12}$ represents the first inter-region difference value of a variance of image convolution of a Gabor filter with a scale of 2 and an angle of 90°, and coef$_{12}$ is 0.048;

collagen_feature$_{13}$ represents the first inter-region difference value of a variance of image convolution of a Gabor filter with a scale of 4 and an angle of 90°, and coef$_{13}$ is 0.12;

collagen_feature$_{14}$ represents the inter-region variation value of a correlation for a pixel displacement of 1 and in an angle of 900 in a gray-level co-occurrence matrix, and coef$_{14}$ is 0.24;

collagen_feature$_{15}$ represents the inter-region variation value of a correlation for a pixel displacement of 2 and in an angle of 135° in a gray-level co-occurrence matrix, and coef$_{15}$ is 0.145; and collagen_feature$_{16}$ represents the inter-region variation value of a correlation for a pixel displacement of 4 and in an angle of 0° in a gray-level co-occurrence matrix, and coef$_{16}$ is 0.303.

After obtaining the collagen score, a doctor may perform prognostic prediction in combination with TNM staging information of the patient and the collagen feature score. The following specific steps 141-142 are included.

In step 141, a survival nomogram is established in combination with TNM staging items and a collagen feature score item.

Figure 4:
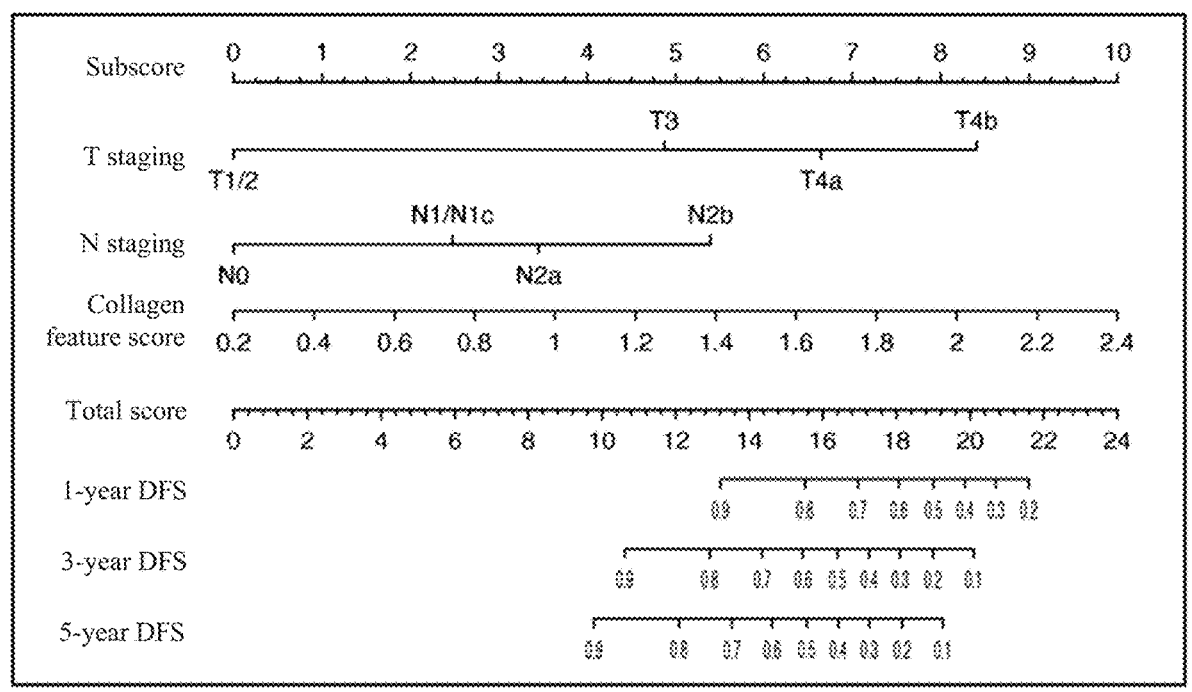
FIG. 4 is a survival nomogram established in combination with a TNM staging item and a collagen feature score item according to the present disclosure.

The survival nomogram established in step 141 is as shown in FIG. 4. The survival nomogram includes a subscore line segment, a T staging line segment, an N staging line segment, a collagen feature score line segment established in parallel, where various scores between 0 and 10 are evenly arranged in the subscore line segment; Tl/2 point, T3 point, T4a point and T4b point in the T staging line segment correspond to points of a score of 0, a score of 4.8, a score of 6.6 and a score of 8.3 in the subscore line segment, respectively; NO point, N1/N1c point, N2a point and N2b point in the N staging line segment correspond to points of the score of 0, a score of 2.5, a score of 3.4 and a score of 5.3 in the subscore line segment, respectively; and various scores between −1.8 and 0.2 are evenly arranged in the collagen feature score line segment, where the point of a score of 0.2 and the point of a score of 2.4 correspond to the point of the score of 0 and the point of a score of 10 in the subscore line segment, respectively.

The survival nomogram further includes a total score line segment, a 1-year DFS line segment, a 3-year DFS line segment and a 5-year DFS line segment established in parallel, where various scores between 0 and 24 are evenly arranged in the total score line segment; points of 0.9, 0.8, 0.7 and 0.6 in the 1-year DFS line segment correspond to points of a score of 12.8, a score of 15.6, a score of 16.8 and a score of 18 in the total score line segment, respectively; points of 0.9, 0.8, 0.7 and 0.6 in the 3-year DFS line segment correspond to points of a score of 10.4, a score of 12.4, a score of 14.4 and a score of 15.2 in the total score line segment, respectively; and points of 0.9, 0.8, 0.7 and 0.6 in the 5-year DFS line segment correspond to points of a score of 9.6, a score of 12, a score of 13.2 and a score of 14.4 in the total score line segment, respectively.

In step 142, a combination of the TNM staging information of the patient and the collagen feature score is introduced into the survival nomogram for prognostic prediction to obtain the DFS of the patient.

For example, the calculated collagen feature score for patient A is 2.305, T staging is T4a, and N staging is N1. By evaluation with the nomogram shown in FIG. 4 according to the collagen feature score and the TNM staging of the patient, it is found that there is a high possibility of post-operative (especially 3 years later) recurrence, metastasis or tumor-related death for the patient, and it is suggested to intensify the frequency of follow-up visits, increase the contents and times of post-operative reexamination and select an aggressive adjunctive treatment strategy.

For example, the calculated collagen feature score for patient B is 0.820, T staging is T3, and N staging is N1. By evaluation with the nomogram shown in FIG. 4 according to the collagen feature score and the TNM staging of the patient, it is found that there is a low possibility of post-operative recurrence, metastasis or tumor-related death for the patient, and it is suggested to carry out conventional follow-up visits and post-operative reexamination and select a conventional adjunctive treatment strategy.

Figure 6:
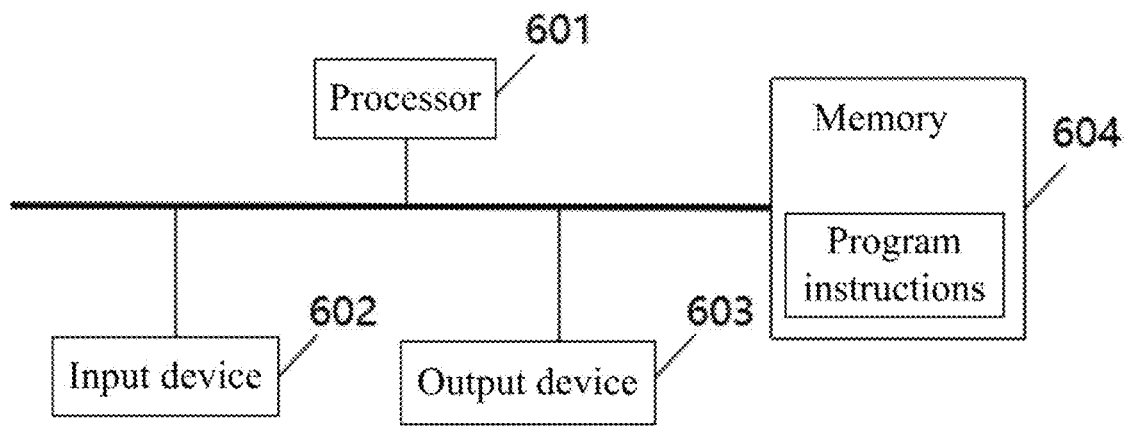
FIG. 6 is a structural schematic diagram of an apparatus for collagen evaluation and prognostic prediction of colorectal cancer provided in the present disclosure.

In the second aspect, the present disclosure provides an apparatus for collagen evaluation and prognostic prediction of colorectal cancer. As shown in FIG. 6, the apparatus for collagen evaluation and prognostic prediction of colorectal cancer includes one or more processors 601, one or more input devices 602, one or more output devices 603 and a memory 604. The processors 601, the input devices 602, the output devices 603 and the memory 604 are connected by a bus. The memory 604 may be the computer readable storage medium as described in any item of the first aspect, and the processors 601 are configured to call the program instructions.

It should be understood that in an embodiment of the present disclosure, the so-called processor 601 may be a central processing unit (CPU); and the processor may also be other general-purpose processors, a digital signal processor (DSP), an application specific integrated circuit (ASIC), a field-programmable gate array (FPGA) or other programmable logic devices, a discrete gate, a transistor logic device, a discrete hardware component, etc. The general-purpose processor may be a microprocessor, or the processor may also be any conventional processor.

The input device 602 may be configured to acquire a multi-photon imaging image of a target imaging region of a histopathological section.

The output device 603 may be configured to output a prognostic prediction obtained by any method of the first aspect to a target terminal for display.

The memory 604 may include a read-only memory (ROM) and a random-access memory (RAM) and may provide instructions and data for the processor 601. A part of the memory 604 may also include a non-volatile RAM. For example, the memory 604 may also store information about a device type.

In a specific implementation, the processor 601, the input device 602 and the output device 603 described in the embodiment of the present disclosure may perform the implementation described by any method of the first aspect, and may also perform the implementation of a terminal device described in an embodiment of the present disclosure, which will not be repeated here.

The above-mentioned computer readable storage medium may be an internal storage unit of the terminal device described in any of the foregoing embodiments, such as a hard disk or an internal storage of the terminal device. The above-mentioned computer readable storage medium may also be an external storage device for the above-mentioned terminal device, such as a plug-in hard disk, a smart media card (SMC), a secure digital (SD) card or a flash card provided for the above-mentioned terminal device. Further, the above-mentioned computer readable storage medium may also include both the internal storage unit and the external storage device for the above-mentioned terminal device. The above-mentioned computer readable storage medium is configured to store the above-mentioned computer program and other programs and data that are required by the above-mentioned terminal device. The above-mentioned computer readable storage medium may also be configured to temporarily store data that has been outputted or will be outputted.

Those of ordinary skill in the art may realize that, units and arithmetic steps of examples described in combination with embodiments provided in the present disclosure can be implemented with electronic hardware, computer software, or a combination thereof. In order to clearly describe the interchangeability between the hardware and the software, compositions and steps of examples have been generally described according to functions in the foregoing descriptions. Whether the functions are performed by hardware or software depends on particular applications and design constraint conditions of the technical solutions. A person skilled in the art may use different methods to implement the described functions for each specific application, but such an implementation should not be considered to be beyond the scope of the present disclosure.

In several embodiments provided in the present disclosure, it should be understood that the disclosed terminal device and method may be implemented in other manners. For example, the described apparatus embodiments are merely examples. For example, the unit division is merely logical function division, and may be other divisions in an actual implementation. For example, a plurality of units or components may be combined or integrated into other apparatus, or some features may be ignored or not performed. In other respects, the mutual coupling or direct coupling or communication connection shown or discussed may be indirect coupling or communication connection through some interfaces, apparatus, or units; or may be implemented in electrical, mechanical, or other forms.

The units described above as separate parts may or may not be physically separated. Parts shown as units may or may not be physical units, which may be located in one position, or may be distributed on a plurality of network units. Some or all of the units may be selected according to actual needs to achieve the objective of the embodiments of the present disclosure.

In addition, functional units in the embodiments of the present disclosure may be integrated into one processing unit, or each of the units may exist alone physically, or two or more of the units are integrated into one unit. The above-mentioned integrated unit may be implemented either in the form of hardware or in the form of a software functional unit.

The above-mentioned integrated unit, if implemented in the form of a software functional unit and sold or used as a stand-alone product, may be stored in a computer-readable storage medium. Based on such understanding, the technical solutions of the present disclosure essentially, or the part contributing to the prior art, or all or part of the technical solutions may be embodied in the form of a software product. The computer software product is stored in a storage medium and includes a plurality of instructions for enabling a computer device (which may be a personal computer (PC), a server, or a network device) to perform all or some steps of the method according to each embodiment of the present disclosure. The storage medium includes any medium capable of storing program codes, such as a USB flash disk, a mobile hard disk, a ROM, a RAM, a magnetic disk, or an optical disk.

Expressions "first", "second", "the first" or "the second" used in various embodiments of the present disclosure may modify various components and are unrelated with the sequence and/or importance. However, these expressions do not limit the corresponding components, but are merely used to distinguishing elements from other elements. For example, a first user device and a second user device indicate different user devices, although both are user devices. For example, without departing from the scope of the present disclosure, a first element may be referred to as a second element, and similarly, a second element may be referred to as a first element.

When an element (such as a first element) is "(operably or communicatively) coupled" with another element (such as a second element) or "(operably or communicatively) coupled to" another element (such as a second element) or "connected to" another element (such as a second element), it should be understood that the element is directly connected to the other element or the element is indirectly connected to the other element via still another element (such as a third element). Conversely, it may be understood that when an element (such as a first element) is "directly connected" or "directly coupled" to another element (such as a second element), there is no element (such as a third element) therebetween.

The above description is merely an illustration of optional embodiments of the present disclosure and the technical principle in use. Those skilled in the art should understand that, the scope of the present disclosure is not limited to the technical solution formed by a specific combination of the foregoing technical features, but should cover other technical solutions formed by any combination of the foregoing technical features or equivalent features thereof without departing from the foregoing inventive concept, for example, a technical solution formed by replacing the foregoing feature with a technical feature having a similar function disclosed in (but not limited to) the present disclosure.

The foregoing descriptions are merely optional embodiments of the present disclosure, and are not intended to limit present disclosure. For those skilled in the art, various modifications and changes may be made to present disclosure. Any modifications, equivalents, improvements, etc. made within the spirit and principle of the present disclosure shall fall within the protection scope of the present disclosure.

What is claimed is:

1. A non-transitory computer readable storage medium storing a computer program, wherein the computer program comprises program instructions that, when executed by a processor, cause the processor to perform following steps:

acquiring a multi-photon imaging image of a target imaging region in a histopathological section, and performing image processing on the multi-photon imaging image to partition the multi-photon imaging image into a center of tumor (CT) region, an invasive margin (IM) region and a normal tissue (N) region;

extracting a value of each collagen feature parameter in each region, and calculating scoring parameters according to the value of each collagen feature parameter, wherein the scoring parameters comprise a mean of each collagen feature parameter in each region, an inter-region difference value and a variation value, wherein the inter-region difference value is a difference between means of each collagen feature parameter for any two regions, and the variation value is a ratio of two inter-region difference values; and the mean of each collagen feature parameter is an average value of a plurality of values of the collagen feature parameter corresponding to a plurality of subregions in a same region of three partitioned regions from the multi-photon imaging image; and selecting the scoring parameters corresponding to target collagen features for collagen feature score calculation, thereby obtaining a collagen feature score of the histopathological section.

2. The non-transitory computer readable storage medium according to claim 1, wherein the performing image processing on the multi-photon imaging image to partition the multi-photon imaging image into a CT region, an IM region and an N region comprises:

extracting a boundary line between a tumor and a normal tissue, and determining a region containing the tumor as an initial CT region and a region containing the normal tissue as an initial N region;

translating the boundary line toward the initial CT region by a first distance to form a first boundary line, and translating the boundary line toward the initial N region by a second distance to form a second boundary line;

determining a region between the first boundary line and the second boundary line as the IM region; and determining a region in the initial CT region other than the IM region as the CT region and a region in the initial N region other than the IM region as the N region.

3. The non-transitory computer readable storage medium according to claim 1, wherein the extracting a value of each collagen feature parameter in each region, and calculating scoring parameters according to the value of each collagen feature parameter comprises:

randomly selecting three CT subregions ROI1, ROI2 and ROI3 in the CT region, and calculating an average value of values of each collagen feature parameter for the three CT subregions as a mean of the corresponding collagen feature parameter of the CT region;

randomly selecting three IM subregions ROI4, ROI5 and ROI6 in the IM region, and calculating an average value of values of each collagen feature parameters for the three IM subregions as a mean of the corresponding collagen feature parameter of the IM region; and randomly selecting three N subregions ROI7, ROI8 and ROI9 in the N region, and calculating an average value of values of each collagen feature parameter for the three N subregions as a mean of the corresponding collagen feature parameter of the N region.

4. The non-transitory computer readable storage medium according to claim 3, wherein the extracting a value of each collagen feature parameter in each region, and calculating scoring parameters according to the value of each collagen feature parameter further comprise:

calculating a difference between means of each collagen feature parameter for the CT region and the IM region as a first inter-region difference value;

calculating a difference between means of each collagen feature parameter for the IM region and the N region as a second inter-region difference value;

calculating a difference between means of each collagen feature parameter for the CT region and the N region as a third inter-region difference value; and deeming a ratio of the first inter-region difference value to the third inter-region difference value as an inter-region variation value.

5. The non-transitory computer readable storage medium according to claim 4, wherein the selecting the scoring parameters corresponding to target collagen features for collagen feature score calculation comprises:

establishing a collagen feature scoring model through a least absolute shrinkage and selection operator (LASSO) regression algorithm as follows:

$$Cf_{score} = \sum_{i=1}^{k} coef_i \cdot \text{collagen\_feature}_i;$$

wherein $Cf_{score}$ represents the collagen feature score; $\text{collagen\_feature}_i$ represents a scoring parameter corresponding to an ith target collagen feature; $coef_i$ represents a calculation coefficient corresponding to the parameter $\text{collagen\_feature}_i$; and k represents a number of the target collagen features.

6. The non-transitory computer readable storage medium according to claim 5, wherein k=16;

$\text{collagen\_feature}_1$ represents a fiber area of the IM region, and $coef_1$ is 0.181;

$\text{collagen\_feature}_2$ represents a fiber number of the IM region, and $coef_2$ is 0.081;

$\text{collagen\_feature}_3$ represents a fiber length of the IM region, and $coef_3$ is 0.303;

$\text{collagen\_feature}_4$ represents a fiber orientation of the N region, and $coef_4$ is −0.515;

$\text{collagen\_feature}_5$ represents the first inter-region difference value of a fiber crosslink density, and $coef_5$ is −0.126;

$\text{collagen\_feature}_6$ represents a correlation for a pixel displacement of 3 and in an angle of 0° in a gray-level co-occurrence matrix of the CT region, and $coef_6$ is 0.018;

collagen_feature$_7$ represents a mean of image convolution of a Gabor filter with a scale of 3 and an angle of 60° for the CT region, and coef$_7$ is 0.477;

collagen_feature$_8$ represents a mean of image convolution of a Gabor filter with a scale of 1 and an angle of 60° for the IM region, and coef$_8$ is −0.119;

collagen_feature$_9$ represents a mean of image convolution of a Gabor filter with a scale of 3 and an angle of 60° for the IM region, and coef$_9$ is 0.232;

collagen_feature$_{10}$ represents a third inter-region difference value of a variance of image convolution of a Gabor filter with a scale of 3 and an angle of 60°, and coef$_{10}$ is 0.016;

collagen_feature$_{11}$ represents a first inter-region difference value of a contrast for a pixel displacement of 3 and in an angle of 45° in a gray-level co-occurrence matrix, and coef$_{11}$ is 0.141;

collagen_feature$_{12}$ represents a first inter-region difference value of a variance of image convolution of a Gabor filter with a scale of 2 and an angle of 90°, and coef$_{12}$ is 0.048;

collagen_feature$_{13}$ represents the first inter-region difference value of a variance of image convolution of a Gabor filter with a scale of 4 and an angle of 90°, and coef$_{13}$ is 0.12;

collagen_feature$_{14}$ represents an inter-region variation value of a correlation for a pixel displacement of 1 and in an angle of 90° in a gray-level co-occurrence matrix, and coef$_{14}$ is 0.24;

collagen_feature$_{15}$ represents an inter-region variation value of a correlation for a pixel displacement of 2 and in an angle of 135° in a gray-level co-occurrence matrix, and coef$_{15}$ is 0.145; and collagen_feature$_{16}$ represents an inter-region variation value of a correlation for a pixel displacement of 4 and in an angle of 0° in a gray-level co-occurrence matrix, and coef$_{16}$ is 0.303.

7. An apparatus for collagen evaluation and prognostic prediction of colorectal cancer, comprising a processor, an input device, an output device and a memory that are connected to one another, wherein the memory comprises the non-transitory computer readable storage medium according to claim 1, and the processor is configured to call the program instructions.

8. The apparatus according to claim 7, wherein
the performing image processing on the multi-photon imaging image to partition the multi-photon imaging image into a CT region, an IM region and an N region comprises:
extracting a boundary line between a tumor and a normal tissue, and determining a region containing the tumor as an initial CT region and a region containing the normal tissue as an initial N region;
translating the boundary line toward the initial CT region by a first distance to form a first boundary line, and translating the boundary line toward the initial N region by a second distance to form a second boundary line;
determining a region between the first boundary line and the second boundary line as the IM region; and
determining a region in the initial CT region other than the IM region as the CT region and a region in the initial N region other than the IM region as the N region.

9. The apparatus according to claim 7, wherein
the extracting a value of each collagen feature parameter in each region, and calculating scoring parameters according to the value of each collagen feature parameter comprises:

randomly selecting three CT subregions ROI1, ROI2 and ROI3 in the CT region, and calculating an average value of values of each collagen feature parameter for the three CT subregions as a mean of the corresponding collagen feature parameter of the CT region;
randomly selecting three IM subregions ROI4, ROI5 and ROI6 in the IM region, and calculating an average value of values of each collagen feature parameters for the three IM subregions as a mean of the corresponding collagen feature parameter of the IM region; and
randomly selecting three N subregions ROI7, ROI8 and ROI9 in the N region, and calculating an average value of values of each collagen feature parameter for the three N subregions as a mean of the corresponding collagen feature parameter of the N region.

10. The apparatus according to claim 9, wherein
the extracting a value of each collagen feature parameter in each region, and calculating scoring parameters according to the value of each collagen feature parameter further comprise:
calculating a difference between means of each collagen feature parameter for the CT region and the IM region as a first inter-region difference value;
calculating a difference between means of each collagen feature parameter for the IM region and the N region as a second inter-region difference value;
calculating a difference between means of each collagen feature parameter for the CT region and the N region as a third inter-region difference value; and
deeming a ratio of the first inter-region difference value to the third inter-region difference value as an inter-region variation value.

11. The apparatus according to claim 10, wherein
the selecting the scoring parameters corresponding to target collagen features for collagen feature score calculation comprises:
establishing a collagen feature scoring model through a least absolute shrinkage and selection operator (LASSO) regression algorithm as follows:

$$Cf_{score} = \sum_{i=1}^{k} coef_i \cdot \text{collagen\_feature}_i;$$

wherein Cf$_{score}$ represents the collagen feature score; collagen_feature$_i$ represents a scoring parameter corresponding to an ith target collagen feature; coef$_i$ represents a calculation coefficient corresponding to the parameter collagen_feature$_i$; and k represents a number of the target collagen features.

12. The apparatus according to claim 11, wherein
k=16;
collagen_feature$_1$ represents a fiber area of the IM region, and coef$_1$ is 0.181;
collagen_feature$_2$ represents a fiber number of the IM region, and coef$_2$ is 0.081;
collagen_feature$_3$ represents a fiber length of the IM region, and coef$_3$ is 0.303;
collagen_feature$_4$ represents a fiber orientation of the N region, and coef$_4$ is −0.515;
collagen_feature$_5$ represents the first inter-region difference value of a fiber crosslink density, and coef$_5$ is −0.126;
collagen_feature$_6$ represents a correlation for a pixel displacement of 3 and in an angle of 0° in a gray-level co-occurrence matrix of the CT region, and coef$_6$ is 0.018;

collagen_feature$_7$ represents a mean of image convolution of a Gabor filter with a scale of 3 and an angle of 60° for the CT region, and coef$_7$ is 0.477;

collagen_feature$_8$ represents a mean of image convolution of a Gabor filter with a scale of 1 and an angle of 60° for the IM region, and coef$_8$ is −0.119;

collagen_feature$_9$ represents a mean of image convolution of a Gabor filter with a scale of 3 and an angle of 60° for the IM region, and coef$_9$ is 0.232;

collagen_feature$_{10}$ represents a third inter-region difference value of a variance of image convolution of a Gabor filter with a scale of 3 and an angle of 60°, and coef$_{10}$ is 0.016;

collagen_feature$_{11}$ represents a first inter-region difference value of a contrast for a pixel displacement of 3 and in an angle of 45° in a gray-level co-occurrence matrix, and coef$_{11}$ is 0.141;

collagen_feature$_{12}$ represents a first inter-region difference value of a variance of image convolution of a Gabor filter with a scale of 2 and an angle of 90°, and coef$_{12}$ is 0.048;

collagen_feature$_{13}$ represents the first inter-region difference value of a variance of image convolution of a Gabor filter with a scale of 4 and an angle of 90°, and coef$_{13}$ is 0.12;

collagen_feature$_{14}$ represents an inter-region variation value of a correlation for a pixel displacement of 1 and in an angle of 90° in a gray-level co-occurrence matrix, and coef$_{14}$ is 0.24;

collagen_feature$_{15}$ represents an inter-region variation value of a correlation for a pixel displacement of 2 and in an angle of 135° in a gray-level co-occurrence matrix, and coef$_{15}$ is 0.145; and collagen_feature$_{16}$ represents an inter-region variation value of a correlation for a pixel displacement of 4 and in an angle of 0° in a gray-level co-occurrence matrix, and coef$_{16}$ is 0.303.

* * * * *